United States Patent [19]

Gallacher et al.

[11] Patent Number: 4,943,656
[45] Date of Patent: Jul. 24, 1990

[54] PROCESS FOR THE PRODUCTION OF POLYALKYLAROMATIC POLYSULFONIC ACIDS AND RECOVERY BY HEAVY PHASE SEPARATION

[75] Inventors: Lawrence V. Gallacher, East Norwalk; Harry N. Condos, Stamford, both of Conn.

[73] Assignee: King Industries, Inc., Norwalk, Conn.

[21] Appl. No.: 632,528

[22] Filed: Jul. 19, 1984

[51] Int. Cl.$^5$ .......................................... C07C 143/24
[52] U.S. Cl. ....................................... 562/90; 562/95; 562/99
[58] Field of Search ................. 260/505 P; 562/90, 95, 562/99

[56] References Cited

U.S. PATENT DOCUMENTS 1,211,923  1/1917  Dennis ............................. 260/505 P
2,764,548  9/1956  King et al. ............................ 252/33
3,957,859  5/1976  Thielcke ............................... 260/505
3,979,478  9/1976  Gallacher ............................. 260/850

FOREIGN PATENT DOCUMENTS 245084  11/1969  U.S.S.R. ........................... 260/505 P

Primary Examiner—Alan Siegel
Attorney, Agent, or Firm—Hedman, Gibson, Costigan & Hoare

[57] ABSTRACT

This invention relates to novel processes for the production of enhanced yields of polyalkylaromatic polysulfonic acids. More particularly, the invention pertains to processes for sulfonating polyalkylaromatic compounds employing sulfuric acid treatment and recovering the polyalkylaromatic polysulfonic acid produced thereby after formation of a three phase system by the addition of controlled amounts of water, causing the polysulfonic acid to accumulate in the bottom layer, with which it is readily separated.

40 Claims, 1 Drawing Sheet

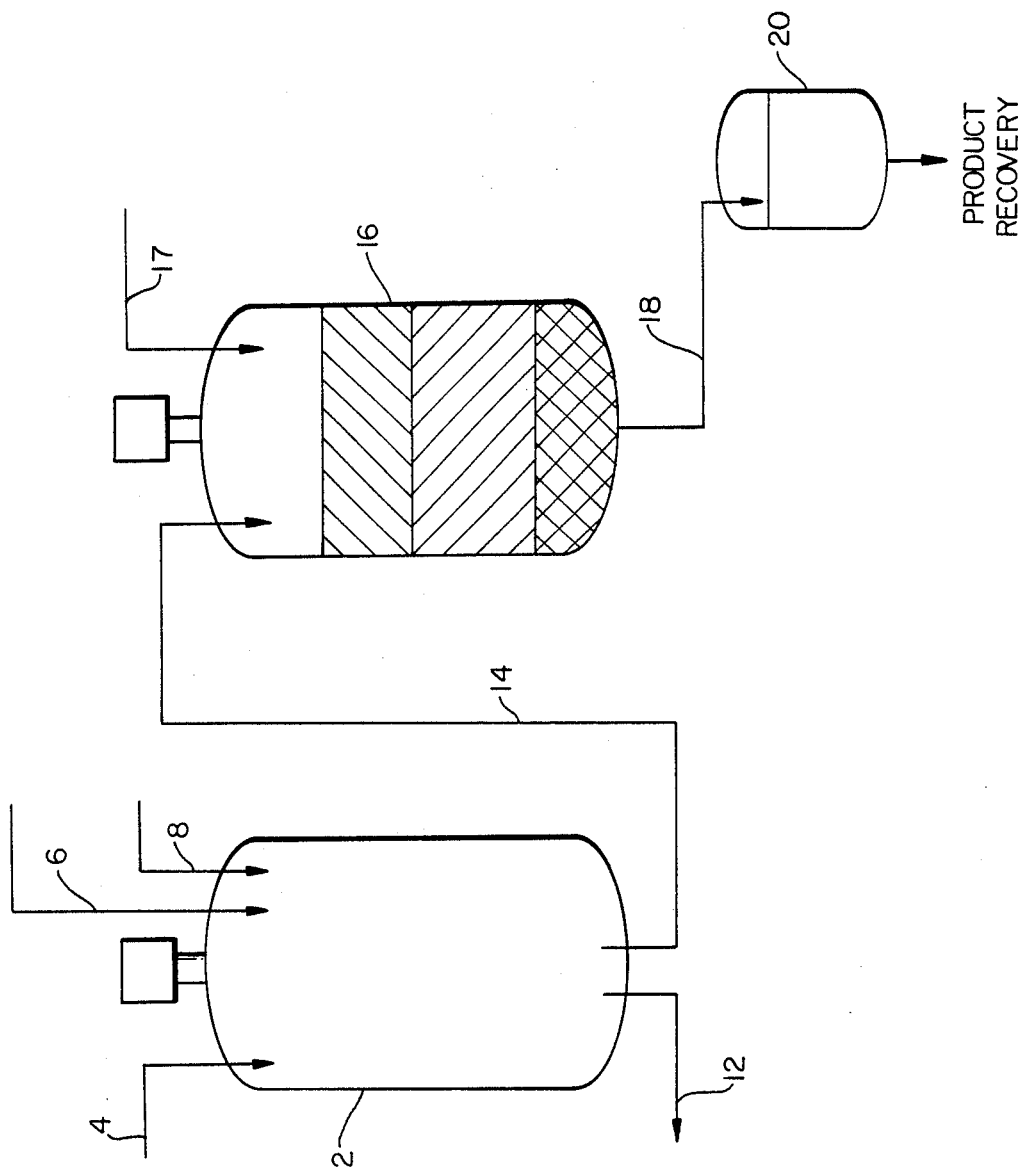

PROCESS FOR THE PRODUCTION OF POLYALKYLAROMATIC POLYSULFONIC ACIDS AND RECOVERY BY HEAVY PHASE SEPARATION

This invention relates to a process for the preparation of polysulfonated organic compounds. More particularly, it is concerned with production of polysulfonic acids by reacting an aromatic compound with sulfuric acid in a solvent, and with a novel multi-phase liquid-liquid extraction process sequence for recovering the sulfonic acids having a preferential water solubility via heavy phase separation.

BACKGROUND OF THE INVENTION

It is often desirable to produce sulfonic acids by reacting an aromatic compound with sulfuric acid, usually in the form of 20% oleum, a mixture of 20% $SO_3$ and 80% $H_2SO_4$. In many cases, this provides two or more aromatic sulfonic acids, at least one of which is preferentially oil soluble and at least one of which is preferentially water soluble. In King and Thielcke, U.S. Pat. No. 2,764,548, there is described a process for the production of dinonylnaphthalene monosulfonic acid. The salts of the monosulfonic acids are relatively highly soluble in oils, and form compositions having exceptional rust-inhibiting properties. It is also disclosed in the patent that the sulfonation of dinonylnaphthalene with sulfuric acid also produces the corresponding disulfonic acid, and this is described to be accumulated in an aqueous layer which is later separated and discarded. Because under common commercial conditions the predominant product is the monosulfonic acid, the disulfonic acid had been treated as a byproduct, and disposed of.

In fact, however, polyalkylaromatic polysulfonic acids, particularly alkylnaphthalene disulfonic acids and their derivatives are very effective in surfactant and catalyst applications. Dinonylnaphthlene disulfonic acid (DNNDSA) in particular is a commercially valuable catalyst in the preparation of coatings based on melamineformaldehyde resins. These applications have been disclosed in U.S. Pat. Nos. 3,979,478, L. V. Gallacher; and 4,200,729, L. J. Calbo, and others.

DNNDSA was reported in the above-mentioned U.S. Pat. No. 2,764,548 to be a by-product in the preparation of dinonylnaphthalene sulfonic acid. This patent describes the removal of the disulfonic acid and sulfuric acid from the monosulfonic acid product by batch-washing with water. Subsequently, in U.S. Pat. No. 3,957,859, Thielcke disclosed a continuous process for recovering DNNDSA from a hydrocarbon solution of mixed sulfonic acids by first extracting countercurrently with water in a multi-stage column and then extracting the aqueous solution countercurrently with a higher alkanol in a second multi-stage column. (As used herein, the term "DNNDSA" is intended to include not only dinonylnaphthalene disulfonic acid, but also mixtures of it with lesser amounts of mononoylnaphthalene disulfonic acid and trinonylnaphthalene disulfonic acid.)

While these techniques are effective in recovering DNNDSA from crude sulfonic acid containing relatively low levels (ca. 1–10% based on the weight of dinonylnaphthalene monosulfonic acid), they are not suitable for high DNNDSA production rates starting with crude sulfonic acid streams containing high levels of DNNDSA.

In order to increase the level of DNNDSA in a crude sulfonic acid based on the sulfonation of dinonylnaphhthalene, it is necessary to increase the mole ratio of sulfonating agent to dinonylnaphthalene in order to increase the level of disulfonation in the product. This can be achieved in a number of ways with different reagents. For example, it can be done by treating a hydrocarbon solution of dinonylnaphthalene with 20% oleum, or, alternately, it may be done by contacting dinonylnaphthalene with a mixture of sulfur trioxide and air in a continuous reactor. This disclosure in no way limits the methods which can be used to prepare crude sulfonic acid mixtures containing relatively large amounts of DNNDSA.

It is an objective of the present invention to provide a novel means of separating high-purity DNNDSA from a crude sulfonic acid mixture comprising DNNDSA, dinonylnaphthalene monosulfonic acid, sulfuric acid, and hydrocarbon solvent.

It has now been discovered that when a crude sulfonic acid mixture containing DNNDSA, dinonylnaphthalene monosulfonic acid, a small amount of dissolved sulfuric acid and hydrocarbon solvent, is mixed with approximately one-half volume of water, and heated to a temperature of approximately 50° C. to 90° C., the mixture separates into three liquid phases: an organic upper layer containing monosulfonic acid and solvent, a middle layer containing sulfuric acid in water, and a lower layer containing primarily DNNDSA and water. Surprisingly, in the preferred embodiment, the lower DNNDSA layer contains approximately one-half or more of the total DNNDSA in the feed at a concentration of approximately 50% in water. Very little sulfuric acid or hydrocarbon solvent are present in this lower layer. Thus, the lower layer can be readily separated and processed directly to yield a high quality DNNDSA concentrate or product.

It has further been discovered that the process is widely applicable to the production of other polyalkylaromatic polysulfonic acids, such as didodecylnaphthalene disulfonic acid and these valuable products are also provided in high purity and high yields.

BRIEF DESCRIPTION OF THE DRAWING

In the drawing is illustrated, in flow diagram form, the arrangement of one suitable type of apparatus for carrying out the process of this invention, and for recovering the products.

SUMMARY OF THE INVENTION

According to the present invention, in its broadest aspects, there is provided a process for the production of enhanced yields of at least one polyalkylaromatic polysulfonic acid comprising:

(a) agitating a mixture of at least one polyalkylaromatic compound, sulfuric acid and a water immiscible, inert diluent having a specific gravity of less than about 1.0;

(b) stratifying said mixture and withdrawing any spent acid layer therefrom;

(c) adding water to the remaining layer in an amount sufficient to form three layers, the bottom layer comprising substantially polyalkylaromatic polysulfonic acid and water; and (d) separating said bottom layer.

According to a preferred aspect of the present invention, there is provided a dual-sulfonation process for the production of enhanced yields of at least one polyalkylaromatic polysulfonic acid comprising:

(a) agitating a mixture of at least one polyalkylaromatic compound, sulfuric acid and a water immiscible, inert diluent having a specific gravity of less than about 1.0;

(b) stratifying said mixture and withdrawing any spent acid layer therefrom;

(c) adding sulfuric acid to the remaining layer and agitating the resulting mixture;

(d) stratifying said mixture and withdrawing any spent acid layer therefrom;

(e) adding water to the remaining layer in an amount sufficient to form three layers, the bottom layer comprising substantially polyalkylaromatic polysulfonic acid and water; and (f) separating said bottom layer.

DETAILED DESCRIPTION OF THE INVENTION

Those skilled in the art of sulfonation are well aware that a wide number of aromatic organic substrates, such as benzene and its analogs, e.g., alkylbenzenes, toluene, the xylenes, polyalkylbenzenes, and higher alkyl mono-, di-, and polysubstituted benzenes, and the corresponding naphthalenes, form sulfonic acids which are preferentially oil soluble (selectively extractible with organic hydrocarbon solvents, and the like), and sulfonic acids which are preferentially water soluble. These are separated from one another by the present invention in its broadest aspects. It is, of course, obvious that a sufficient number of ring positions will remain unsubstituted on the aromatic nucleus to provide sulfonation sites. Polyalkyl aromatic compounds having 0 or 1 aromatic carbon-hydrogen groups are wholly unsuitable as substrates. Preferably, the molecular weight of the substrate will be above about 350.

In carrying out step (a) in the above process there can be used a polyalkylaromatic compound capable of being sulfonated by agitating with sulfuric acid, with oleum, with sulfur trioxide and air or other equivalents. In a preferred embodiment the use of polyalkylaromatic compounds which are naphthalene compounds is contemplated. In another preferred embodiment, the alkyl group of the polyalkylaromatic compound is selected from octyl, nonyl, decyl, undecyl and dodecyl or mixtures of any of the foregoing; more preferably, the alkyl group is highly branched. In its more preferred embodiments, the polyalkyalaromatic compounds are selected from the group of dinonylnaphthalenes or didodecylnaphthalenes; most preferred are such substituted naphthalenes having highly branched nonyl groups.

As mentioned above, the sulfuric acid, when used herein, includes oleum, $SO_3$ and air, and the like. The sulfonating acid can be used in widely varying amounts and/or concentrations but preferably at least sufficient to provide a mole-ratio of active sulfonating agent to polyalkylaromatic compound of at least 1.1:1. Preferably, the mole-ratio is in the range of 1.5:1 to about 2.5:1. With a single sulfonation, the minimum mole ratio is not less than about 1.3:1.

In the process of sulfonation carried out in step (a) and, optionally in the preferred embodiment, step (c), the polyalkyl polyaromatic naphthalene compound is dissolved in a solvent which is substantially free of aromatics or olefins which under the conditions of the reaction would disadvantageously react with the sulfonating acid, e.g., sulfuric acid. The use of a solvent for the polyalkylaromatic compound during the sulfonation reaction is necessary to maintain the reaction in the liquid state, so that the sulfonating acid and the substrate napthalene may be thoroughly mixed during the sulfonation. After sulfonation, the presence of the solvent in sufficient quantity maintains the polysulfonic acid in the liquid state and allows separation of any spent acid layer from the solvent layer, containing the polyalkylaromatic polysulfonic acid by stratification.

In order to permit separation of any spent acid layer, a diluent having the above-mentioned physical/chemical properties and a specific gravity of less than about 1.0, should be selected. Preferably, the solvent will have a specific gravity of about 0.7 to about 0.8. Most preferred diluents for almost any polyalkylaromatic compound in the sulfonation reaction are petroleum naphtha, hexane, heptane, octane and mixtures of such diluents.

The lower the specific gravity of the diluent for the polyalkylaromatic compound, the more easily and completely will the stratification between the organic phase and the spent acid phase occur.

After stratification and withdrawal of any spent acid layer, water is added in an amount sufficient to form three layers. The three-layer system is formed as follows: The single, organic phase remaining after the acid withdrawal comprising the diluent, mono- and polysulfonic acids, a minor amount of unseparated sulfuric acid and some impurities and reaction by-products has water added to it.

While not intending to be bound by any theory, it appears that water performs at least several functions: First, it extracts a major portion of the polysulfonic acid products, probably in the form of hydrates. Second, it extracts the minor amount of residual sulfuric acid, and, in the case of oleum, or air/$SO_3$, solubilizes the residual sulfur trioxide as sulfuric acid. When added in a sufficient amount, the water causes the formation of a substantially sulfuric acid solution middle layer, and a substantially polysulfonic acid-containing substantially aqueous bottom layer. This is achieved when the amount of water added extracts from the organic phase the quantity of unseparated sulfuric acid sufficient to result in the formation of an about 7 percent sulfuric acid solution. A sulfuric acid solution of about this concentration or higher inhibits the solubility of the polysulfonic acid therein and as a result the acid is concentrated in a more dense essentially aqueous bottom layer. If the quantity of the sulfuric acid extracted from the organic phase results in the formation of a sulfuric acid solution of about 12 percent concentration or greater the sulfuric acid solution is more dense than the di- and polysulfonic-containing substantially aqueous solution and will form the bottom layer, or will not stratify in relation to the polysulfonic acid-containing substantially aqueous solution. Preferably, the amount of water added in the three-layer forming step is sufficient to result in the formation of a middle layer which contains from about 7 to about 12 percent sulfuric acid. In another preferred embodiment, the amount of water added is from about 0.4 to about 0.6 times the volume of the solution remaining after the spent acid is withdrawn.

As has been mentioned, in the most preferred embodiments, the organic phase remaining after stratifying and withdrawing any spent sulfuric acid in step (b) is again agitated with an additional amount of sulfuric acid, i.e., double treated. After again adding the sulfuric acid and agitating the mixture produced thereby, the remaining steps of the process remain essentially unchanged. This double treatment process results in especially enhanced yields of polysulfonic acid.

While not essential, it is preferred to maintain the temperature in the heavy phase (steps (e) and (f)) sufficiently high to prevent solidification of the polyalkylaromatic polysulfonic acid in the bottom layer. This will depend on the nature of the material, but in general will be moderately elevated, e.g., 55° to 75° C. and preferably 60° to 70° C.

The polysulfonic acids can be recovered in a number of ways, usually dictated by the ultimate use of the product. In one manner of proceeding, the heavy phase concentrate is neutralized directly by the addition of 20% aqueous caustic soda to form a composition with surfactant properties. Alternatively, a lower aliphatic alcohol may be added to form a composition useful as a catalyst for amino resins.

DESCRIPTION OF THE PREFERRED EMBODIMENTS

Referring to the drawing, sulfonation reactor 2 is fitted with an agitator, coils for cooling and heating and conduits 4, 6 and 8 for introduction, respectively, of a mixture of a polyalkylaromatic compound in a suitable diluent, more diluent and sulfuric acid, respectively. In one way of proceeding, the solution of the polyalkylaromatic compound is added, followed by a suitable quantity of sulfuric acid. The mixture is agitated and reacted at a temperature of 10° to 65° C., preferably 25° to 55° C. for one to three hours, until the sulfonation step is about finished. Then agitation is stopped, and the mixture is allowed to stratify, i.e., separate into two phases, an organic phase and any lower spent acid phase. Any acid phase is separated, e.g., by withdrawal through line 12 to a spent acid holding tank (not shown). At this point, optionally, but preferably, a second quantity of sulfuric acid is added through inlet 8 and the agitation, separation and withdrawal steps are repeated. When the sulfuric acid sulfonation additions and withdrawals are completed, and preferably after transferring the organic phase through conduit 14 to settling and wash tank 16, water is added through conduit 17, in controlled amounts, as will be described later. The water/organic mixture is agitated in tank 16, and, after agitation is stopped the mixture separates quickly into the three layers previously described. The heavy bottom phase is withdrawn, e.g. through conduit 18 to product storage vessel 20.

The following non-limiting examples were carried out on a laboratory scale and on a plant scale in suitable equipment known to those skilled in the art with the results set forth, and summarized in tabular form hereinafter.

EXAMPLE 1

Three hundred and sixteen grams of a 48% solution by weight of dinonylnaphthalene in heptane was treated with two 113 gram portions of 20% oleum in a laboratory reaction flask. Each addition took approximately 1½ hours. During the reaction the temperature ranged from 26° C. at the start to a maximum of 37° at the end of the first addition. After the first oleum addition was complete, the spent acid was drawn off and saved. At the conclusion of the second oleum addition, the first half of the spent acid was recombined with the contents of the reaction flask and the entire mixture was treated with 11 milliliters of H$_2$O. The spent acid was then allowed to settle, and 205 grams were removed, leaving 337 grams of crude sufonic acid in heptane.

The crude product was then heated to 71° C. and 375 grams of water preheated to the same temperature were added and mixed. The mixture separated quickly to yield a three-phase system: an organic top layer, an aqueous middle layer, and a darker viscous lower layer. 53.2 grams of lower layer were recovered and titrated, showing a DNNDSA content of 48%. This heavy lower phase solidified on cooling.

The remaining organic was washed several times with water. The extracts were found to contain 24.4 grams of DNNDSA, or approximately half of the total DNNDSA. The total DNNDSA yield was 49.8 grams.

EXAMPLE 2

On a plant scale, 1175 gallons of dinonylnaphthalene in heptane containing 4137 pounds of DNN were sulfonated in two treats with 196 gallons of 20% oleum per treat. After the first oleum addition, the spent acid was removed. After both oleum additions were complete, all of the spent acid was recombined with the product, and 147 gallons of heptane and 34 gallons of water were added and mixed in. After the spent acid was allowed to settle and was drawn off, 700 gallons of water and 15 gallons of 35% hydrogen peroxide were added and mixed. The heavy phase contained 1205 pounds of DNNDSA as 51.2% DNNDSA in water containing 0.5% sulfuric acid and less than 0.5% heptane. The wash water plus the water from two succeeding washes contained a total of 233 pounds of 100% DNNDSA.

EXAMPLE 3

In Examples 1 and 2 the mole ratio of available SO$_3$ in the 20% oleum to dinonylnaphthalene was held to 1.5:1. In this example, the ratio was increased to 1.8:1. 900 gallons of a 52% solution of dinonylnapthalene in heptane were treated with 20% oleum in two equal treats, so that the ultimate ratio of SO$_3$ to DNN was 1.8:1. After the first oleum addition, the spent acid was removed. After the second addition, 320 gallons of heptane were added, and the entire mixture of heptane, product, spent acid were agitated for one hour. The batch was then allowed to settle and the spent acid was drawn off. 30 gallons of 35% aqueous hydrogen peroxide and 600 gallons of water were then added and mixed with the batch. The heavy phase quickly separated and was drawn off into a second mixing tank. It was found that the heavy phase contained 57% DNNDSA in water, with approximately 1% combined sulfuric acid and neglible heptane. The total DNNDSA in the heavy phase was approximately 1180 pounds. An additional 400 pounds of DNNDSA was recovered from the first wash and a subsequent water wash of the same volume.

EXAMPLE 4

This example shows the feasibility of producing a heavy-phase concentrate of didodecylnaphthalene disulfonic acid using the double-sulfonation and controlled washing technique described above. 211 grams of didodecylnaphthalene synthesized by the alkylation of naphthalene with tetrapropylene using aluminum chloride catalyst and nitrobenzene solvent was diluted with an equal weight of heptane. This solution of "DDN" in heptane was sulfonated in two treats with 122 grams of 20% oleum per treat. After each oleum treat, the spent acid was allowed to separate and was then drawn off. The sulfonation was carried out at a temperature of 40° C. The overall mole ratio of available SO₃ to alkylate was approximately 2.0:1. 441 grams of crude sulfonic acid in heptane was recovered from the reaction. 110 milliliters of heptane and 270 milliliters of hot water were added to the crude sulfonic acid in a separatory funnel and mixed well. On standing, a dense heavy-phase settled to the bottom. It contained 56.1% didodecylnaphthalene sulfonic acid in a total weight of 34.3 grams. the upper organic layer was washed several times with water. All of the washes including the heavy-phase wash were combined and yielded an additional 20.4 grams of disulfonic acid for a total yield of 39.6 grams of didodecylnaphthalene disulfonic acid.

The results of the foregoing examples are set forth in Table 1:

TABLE 1

| Example | Mole-Ratio Available $SO_3{}^c$ Polyalkylaromatic Starting Material | % Solution of Polyalkylaromatic Polysulfonic Acid in Heavy Phase | Ratio Polyalkylaromatic Polysulfonic acid$^b$ to Polyalkylaromatic Starting Material$^b$ |
|---|---|---|---|
| A. Prior Art | 0.85 | No Heavy Phase | 0.04:1 |
| 1. Laboratory Scale | 1.5:1 | 48 | 0.33:1 |
| 2. Plant Scale | 1.5:1 | 51.2 | 0.34:1 |
| 3. Plant Scale | 1.8:1 | 57 | 0.42:1 |
| 4. Laboratory Scale | 2.0:1 | 56.1 | 0.19:1$^d$ |

$^a$Dinonylnaphthalene
$^b$Dinonylnaphthalene disulfonic acid
$^c$In 20% oleum
$^d$Didodecylnaphthalene to didodecylnaphthalene disulfonic acid

EXAMPLE 5

The general procedure of Example 4 was repeated, but substituting dinonylnaphthalene for didodecylnaphthalene, and an overall mole ratio of active sulfonating agent to polyalkylaromatic of 1.1:1 was used. Following treatment of 400 g. of a 50% solution of dinonylnaphthalene in heptane with 20% oleum in two 110 gram treats, 411 g. of crude sulfonic acid solution was separated and recovered. Two hundred grams of 80° C. water was added, mixed and settled. Ten grams of heavy phase separated, containing 54.7% of DNNDSA. The aqueous phase plus 2 additional washes contained 38 g. of additional DNNDSA. This demonstrates the minimum mole ratio necessary to obtain heavy phase formation in a double sulfonation process in accordance with this invention.

EXAMPLE 6

The procedure of Example 5 was repeated, but using only a single oleum treat. The mole ratio in this instance was 1.3:1. Three hundred grams of 50% dinonylnaphthalene in heptane was sulfonated at 40° C. with 190 g. of 20% oleum in one treat, 313.7 g. of crude sulfonic acid were recovered. One-half volume of 80° C. water was added, mixed and settled. Seven and two-tenths grams of heavy phase containing 52% of DNNDSA separated. The aqueous phase plus additional washes contained another 10.8 grams of DNNDSA. This demonstrates the minimum mole ratio necessary to obtain heavy phase formation in a single sulfonation process in accordance with this invention.

The foregoing examples demonstrate, in comparison with the prior art, that the process of the present invention provides a vastly improved yield of polyalkylaromatic polysulfonic acids in relatively pure form which can be converted directly to useful products without the need for complicated purification and/or concentration steps.

The foregoing patents are incorporated herein by reference. Obviously, many variations will suggest themselves to those skilled in this art in light of the above detailed description. For example, instead of heptane as a diluent, isooctane can be used; instead of oleum, SO₃ and air or chlorosulfonic acid can be used as active sulfonating agents; instead of dinonylnaphthalene or didodecylnapthalene, dioctylnaphthalene or dinonyl anthracene can be used. All such obvious variations are within the full intended scope of the appended claims.

What is claimed is:

1. A process for the production of a polyalkylaromatic polysulfonic acid comprising:
   (a) agitating a mixture of at least one polyalkylaromatic compound, sulfuric acid and a water immiscible, inert diluent having a specific gravity of less than about 1.0;
   (b) stratifying said mixture and withdrawing any spent acid layer therefrom;
   (c) adding water to the remaining layer in an amount sufficient to form three layers, the bottom layer comprising substantially polyalkylaromatic polysulfonic acid and water; and
   (d) separating said bottom layer.

2. A process as defined in claim 1 wherein the alkyl group of the polyalkylaromatic compound is selected from octyl, nonyl, decyl, undecyl and dodecyl or mixtures of any of the foregoing.

3. A process as defined in claim 2 wherein the alkyl groups are highly branched.

4. A process as defined in claim 1 wherein the polyalkylaromatic compound is a naphthalene compound.

5. A process as defined in claim 1 wherein the mole-ratio of the sulfuric acid to the polyalkylaromatic compound is not substantially less than about 1.1:1.

6. A process as defined in claim 5 wherein said mole ratio is in the range of 1.5:1 to about 2.5:1.

7. A process as defined in claim 1 wherein said diluent has a specific gravity in the range of from about 0.7 to about 0.8.

8. A process as defined in claim 1 wherein said diluent is selected from naphtha, hexane, heptane, octane or a mixture of any of the foregoing.

9. A process as defined in claim 1 wherein the amount of water added in step (c) is from about 0.4 to about 0.6 times the volume remaining after step (b).

10. A process as defined in claim 1 wherein the amount of water added is sufficient to result in the formation of a middle layer which contains from about 7 to about 12 per cent sulfuric acid.

11. A process as defined in claim 1 wherein the temperature in steps (c) and (d) is maintained sufficiently high to prevent solidification of the polyalkylaromatic polysulfonic acid in said bottom layer.

12. A process as defined in claim 1 wherein the polyalkylaromatic polysulfonic acid produced thereby has a molecular weight of greater than about 350.

13. A process for the production of a polyalkylaromatic polysulfonic acid comprising:
(a) agitating a mixture of at least one polyalkylaromatic compound, sulfuric acid and a water immiscible, inert diluent having a specific gravity of less than about 1.0;
(b) stratifying said mixture and withdrawing any spent acid layer therefrom;
(c) adding sulfuric acid to the remaining layer and agitating the resulting mixture;
(d) stratifying said mixture and withdrawing any spent acid layer therefrom;
(e) adding water to the remaining layer in an amount sufficient to form three layers, the bottom layer comprising substantially polyalkylaromatic polysulfonic acid and water; and
(f) separating said bottom layer.

14. A process as defined in claim 13 wherein the alkyl group of the polyalkylaromatic compound is selected from octyl, nonyl, decyl, undecyl and dodecyl or mixtures of any of the foregoing.

15. A process as defined in claim 14 wherein the alkyl groups are highly branched.

16. A process as defined in claim 13 wherein the polyalkylaromatic compound is a naphthalene compound.

17. A process as defined in claim 13 wherein the mole-ratio of the sulfuric acid to the polyalkylaromatic compound in steps (a) and (c) is not substantially less than about 1.1:1.

18. A process as defined in claim 17 wherein said mole ratio is in the range of 1.5:1 to about 2.5:1.

19. A process as defined in claim 13 wherein said diluent has a specific gravity in the range of from about 0.7 to about 0.8.

20. A process as defined in claim 13 wherein said diluent is selected from naphtha, hexane, heptane, octane or a mixture of any of the foregoing.

21. A process as defined in claim 13 wherein the amount of water added in step (e) is from about 0.4 to about 0.6 times the volume remaining after step (d).

22. A process as defined in claim 13 wherein the amount of water added in step (e) is sufficient to result in the formation of a middle layer which contains from about 7 to about 12 per cent sulfuric acid.

23. A process as defined in claim 13 wherein the temperature in steps (e) and (f) is maintained sufficiently high to prevent solidification of the polyalkylaromatic polysulfonic acid in said bottom layer.

24. A process as defined in claim 13 wherein the polyalkylaromatic polysulfonic acid produced thereby has a molecular weight of greater than about 350.

25. A process for the production of a dinonylnaphthalene disulfonic acid comprising:
(a) agitating a mixture of at least one dinonylnaphthalene compound, sulfuric acid and a water immiscible, inert diluent having a specific gravity of less than about 1.0;
(b) stratifying said mixture and withdrawing any spent acid layer therefrom;
(c) adding water to the remaining layer in an amount sufficient to form three layers, the bottom layer comprising substantially dinonylnaphthalene disulfonic acid and water; and
(d) separating said bottom layer.

26. A process as defined in claim 25 wherein the nonyl group is highly branched.

27. A process as defined in claim 25 wherein the mole-ratio of the sulfuric acid to the dinonylnaphthalene compound is not substantially less than about 1.3:1.

28. A process as defined in claim 25 wherein said diluent has a specific gravity in the range of from about 0.7 to about 0.8.

29. A process as defined in claim 25 wherein said diluent is selected from naphtha, hexane, heptane, octane or a mixture of any of the foregoing.

30. A process as defined in claim 25 wherein the amount of water added in step (c) is from about 0.4 to about 0.6 times the volume remaining after step (b).

31. A process as defined in claim 25 wherein the amount of water added is sufficient to result in the formation of a middle layer which contains from about 7 to about 12 percent sulfuric acid.

32. A process as defined in claim 25 wherein the temperature in steps (c) and (d) is maintained sufficiently high to prevent solidification of the dinonylnaphthalene disulfonic acid in said bottom layer.

33. A process for the production of a dinonylnaphthalene disulfonic acid comprising:
(a) agitating a mixture of at least one dinonylnaphthalene compound, sulfuric acid and a water immiscible, inert diluent having a specific gravity of less than about 1.0;
(b) stratifying said mixture and withdrawing any spent acid layer therefrom;
(c) adding sulfuric acid to the remaining layer and agitating the resulting mixture;
(d) stratifying said mixture and withdrawing any spent acid layer;
(e) adding water to the remaining layer in an amount sufficient to form three layers, the bottom layer comprising substantially dinonylnaphthalene disulfonic acid and water; and
(f) separating said bottom layer.

34. A process as defined in claim 33 wherein the nonyl group is highly branched.

35. A process as defined in claim 33 wherein the mole-ratio of the sulfuric acid to the dinonylnaphthalene compound in steps (a) and (c) is from not substantially less than about 1.5:1 to not substantially greater than about 2.5:1.

36. A process as defined in claim 33 wherein said diluent has a specific gravity in the range of from about 0.7 to about 0.8.

37. A process as defined in claim 33 wherein said diluent is selected from naphtha, hexane, heptane, octane or a mixture of any of the foregoing.

38. A process as defined in claim 33 wherein the amount of water added in step (e) is from about 0.4 to about 0.6 times of the volume remaining after step (d).

39. A process as defined in claim 33 wherein the amount of water added in step (e) is sufficient to result in the formation of a middle layer which contains from about 7 to about 12 per cent sulfuric acid.

40. A process as defined in claim 33 wherein the temperature in steps (e) and (f) is maintained sufficiently high to prevent solidification of the dinonylnaphthalene disulfonic acid in said bottom layer.

* * * * *